(12) United States Patent
Larkin

(10) Patent No.: US 7,055,533 B2
(45) Date of Patent: Jun. 6, 2006

(54) APPARATUS AND METHOD FOR CLEANING HVE CONDUITS

(76) Inventor: Rodney B. Larkin, 1751 S. Redwood Rd., Woods Cross, UT (US) 84087

( * ) Notice: Subject to any disclaimer, the term of this patent is extended or adjusted under 35 U.S.C. 154(b) by 591 days.

(21) Appl. No.: 10/322,220

(22) Filed: Dec. 17, 2002

(65) Prior Publication Data

US 2004/0112407 A1    Jun. 17, 2004

(51) Int. Cl.
*B08B 9/032* (2006.01)
*B08B 9/035* (2006.01)

(52) U.S. Cl. ............... 134/22.12; 134/22.11; 134/166 R; 134/166 C; 134/167 C

(58) Field of Classification Search ............ 134/22.1, 134/22.12, 22.18, 34, 37, 166 R, 166 C, 134/172, 178, 99.2, 100.1, 102.1, 102.2, 134/22.11, 167 C
See application file for complete search history.

(56) References Cited

U.S. PATENT DOCUMENTS

| | | | |
|---|---|---|---|
| 3,833,417 A * | 9/1974 | Griparis | 134/22.12 |
| 4,209,343 A * | 6/1980 | Lane et al. | 134/22.12 |
| 4,668,190 A | 5/1987 | Overmyer | |
| 4,902,352 A * | 2/1990 | Christian | 134/22.12 |
| 4,923,522 A * | 5/1990 | Sowers | 134/22.1 |
| 5,308,579 A | 5/1994 | Melon et al. | |
| 5,492,672 A | 2/1996 | Childers et al. | |
| 5,556,607 A | 9/1996 | Childers et al. | |
| 5,709,546 A | 1/1998 | Waggoner | |
| 5,785,527 A | 7/1998 | Jensen et al. | |
| 5,837,204 A | 11/1998 | Prevost et al. | |
| 6,027,572 A | 2/2000 | Labib et al. | |
| 6,039,060 A | 3/2000 | Rower | |
| 6,250,920 B1 | 6/2001 | Overmyer | |
| 6,408,861 B1 * | 6/2002 | Ortega | 134/100.1 |
| 6,423,219 B1 | 7/2002 | Chandler | |
| 6,858,021 B1 * | 2/2005 | Washington | 604/265 |
| 2001/0052355 A1 * | 12/2001 | Hoenisch et al. | 134/123 |

* cited by examiner

*Primary Examiner*—Alexander Markoff
(74) *Attorney, Agent, or Firm*—Brian C. Trask

(57) ABSTRACT

An apparatus for dispensing misted cleaning or disinfecting solution at one or more atomizing discharge ports for cleaning suction conduits, such as HVE conduits. The apparatus includes a venturi valve to extract concentrated cleaning/disinfectant fluid from a storage container. The concentrated fluid is mixed with a pressurized venturi-operating fluid, typically water, before being suctioned through an atomizing discharge port and entering the conduit to be cleaned.

18 Claims, 1 Drawing Sheet

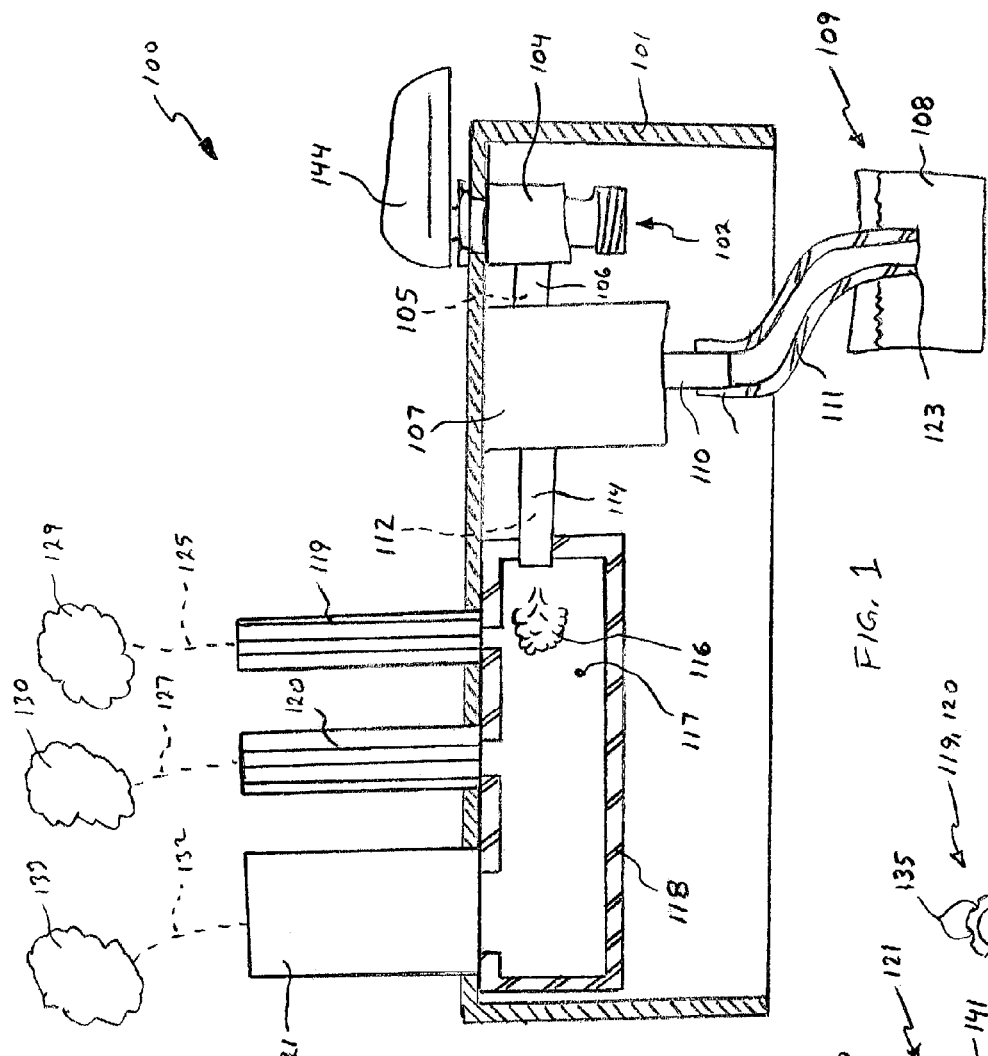

APPARATUS AND METHOD FOR CLEANING HVE CONDUITS

BACKGROUND

1. Field of the Invention

The invention relates generally to an apparatus and method for cleaning, disinfecting, and/or sterilizing conduits, and particularly to cleaning conduits in High Volume Evacuation (HVE) systems, such as those HVE systems found in dental operatories.

2. State of the Art

Dental operatories contain various conduits and equipment to suction debris and fluids from a patient's mouth during tooth cleaning, general dental procedures, and surgical procedures. The various conduits and equipment require periodic flushing or cleaning to resist a buildup of micro-organisms and debris inside the lumens of the dental apparatus. A variety of fluid supply devices have been developed to facilitate cleaning of interior surfaces of the water conduits and equipment. Several of such devices are disclosed in patent literature, including U.S. Pat. No. 4,668,190; U.S. Pat. No. 5,308,579; U.S. Pat. No. 5,492,672; U.S. Pat. No. 5,556,607; U.S. Pat. No. 5,709,546; U.S. Pat. No. 5,785,523; U.S. Pat. No. 5,837,204; U.S. Pat. No. 6,027,572; U.S. Pat. No. 6,039,060; U.S. Pat. No. 6,250,920; and/or U.S. Pat. No. 6,423,219.

Certain patents (e.g. '190; '523; and '060) disclose the use of venturi devices to withdraw solutions from holding containers. Melon in '579 discloses distributing liquids in liquid form to handpieces, then atomizing the fluid in the handpiece using compressed air. Some references use an entirely different set-up to disinfect dental lines (e.g. Prevost et al. in '204 who disclose pressurized disinfectant solution and a check valve arrangement; and Labib et al. in '572 who teach use of turbulent flow inside the tube.) However, none of the references are believed to contemplate the use of both a venturi device and an atomizing device in combination to better mix and apply atomized or misted cleaning solution to the interior of suction conduits.

BRIEF SUMMARY OF THE INVENTION

The present invention provides an apparatus and method for cleaning and/or disinfecting interior surfaces of conduits. The invention has particular application to cleaning suction hoses and passages through interconnected equipment in a HVE system, such as might be found in a dental operatory.

A device constructed according to principles of the invention generally includes: a first valve to control flow of a pressurized fluid (typically water), a venturi valve, and an atomizing nozzle arranged in fluid communication through the venturi with the first valve. A housing typically is provided to hold the individual components in a location relative to suspending structure, such as a wall. The housing can protect the components from damage, facilitate connection of the device to a conduit to be cleaned, and provide an easily cleaned surface.

A container is provided to hold concentrated cleaning or disinfecting fluid for transfer of that fluid by a siphon tube to a suction orifice of the device's venturi valve. At the venturi, the concentrated cleaning fluid is at least partially mixed with the water, or other fluid, from the pressurized fluid supply. Downstream of the venturi, the mixed fluids are discharged into a distribution manifold. The interior of the manifold typically defines a first volume in which to receive the discharged fluid mix, thereby promoting additional mixing of the two fluids.

In general, the distribution manifold provides at least one discharge port that is configured and arranged to receive a conduit for purpose of supplying cleaning fluid into the conduit. A plurality of discharge ports may be provided in certain devices. In devices providing a plurality of discharge ports, each discharge port is constructed to be in fluid communication with the volume inside the manifold. Typically, a surface of a discharge port is adapted to admit bypass air to augment a volumetric flow suctioned into the conduit. Such discharge ports effectively act as atomizing nozzles, entraining air or bubbles into the mixed cleaning fluid. For purpose of this disclosure, such aerated cleaning fluid may be regarded as a mist, and is believed to provide enhanced cleaning.

The first valve, being adapted to permit or restrict flow of the pressurized water or other fluid, can be a manual on/off valve, or an automatically activated valve. In one workable arrangement, an automatic valve can be configured to be activated by placement of a suctioning conduit into a receiving position with respect to a discharge port.

Certain embodiments of the invention may include a shut-off valve disposed to occlude a discharge port. One desirable and workable shut-off valve is automatically opened to permit flow of misted cleaning fluid by placement of a conduit into mating reception with a discharge port on which the shut-off valve is installed. Another workable shut-off valve can be arranged as a stopper, or cap, configured substantially to occlude a discharge port.

One method for using the apparatus to clean a conduit includes providing a device constructed according to principles of the invention at a cleaning location. Then, a suction conduit is placed into mating reception with a discharge port of the device. Suction is applied to the suction conduit to be cleaned, and a valve operating the device is opened for a time interval sufficient to clean that suction conduit. In an automated cleaning method, one or more conduits may be placed in a stored position in engagement with one or more corresponding discharge port(s). A mist control valve and one or more suction control valve(s) disposed to provide suction through a conduit may then automatically be actuated according to a desired cleaning schedule. Actuation of the valves may be programmed to occur as desired.

BRIEF DESCRIPTION OF THE DRAWINGS

In the drawings, which illustrate what is currently considered to be the best mode for carrying out the invention:

FIG. 1 is a side view in elevation, partially in section, of the currently preferred embodiment of the invention;

FIG. 2 is a top view of a first discharge port of the embodiment illustrated in FIG. 1; and FIG. 3 is a top view representative of second and third discharge ports of the embodiment illustrated in FIG. 1.

DETAILED DESCRIPTION OF THE ILLUSTRATED EMBODIMENT

FIG. 1 illustrates a currently preferred embodiment, generally indicated at 100, of a dispensing apparatus adapted to deliver a cleaning solution in a misted form to one or more suctioning conduits. A housing 101 generally is provided to hold the components of the device 100 in a fixed relation to a holding structure, such as a wall, stand, piece of equipment, or any other conveniently located and operable support structure. Illustrated housing 101 is operable to contain certain components of the device 100 inside an attractive and easily cleanable package.

A pressurized first fluid source can be attached at fitting 102 of an on/off valve 104. A workable pressurized first fluid source includes tap water 105 commonly available as a plumbing utility. Alternative first fluids can include solvents, detergents, or mixtures of a plurality of fluids. For simplicity during the remainder of this disclosure, the pressurized first fluid source will be assumed to be water. It should also be noted that connections between components of device 100 are, in general, ordinary threaded connections in accordance with conventional plumbing fittings, and so may not be illustrated in detail. However, connections between components may be effected in any desired manner, including press fits, threads, solder, and adhesive bonds.

A length of connecting conduit 106 is affixed in fluid-flow communication between an outlet of valve 104 and an inlet of a venturi valve 107. One operable venturi valve is sold by Dema of St. Louis, Mo., under the part No. 201C. Concentrated cleaning and/or disinfecting fluid 108 stored in container 109 can be drawn into suction end 110 of venturi valve 107 through a siphon tube 111 when valve 104 is opened. Subsequent to entering the venturi valve 107, the suctioned fluid 108 then at least partially mixes with the water 105 from conduit 106. The fluid mixture 112 then passes through length of connecting conduit 1 14 for discharge as a mixed fluid 116 into a space 117 defining a volume interior to atomizing manifold 118.

Fluid mixture 112 travelling through conduit 114 is expelled into volume 117 inside manifold 118. Volume 117 provides an additional opportunity for agitation of fluid 112 to further and more completely mix the cleaning fluid 108 and pressurized water 105 to form mixed fluid 116. The mixed fluid 116 can then pass from manifold 118 into one or more atomizing conduit connectors, such as illustrated discharge ports 119–121. It is within contemplation for manifold 118 directly to constitute a discharge port, such as one or more of ports 119–121.

It is believed that fluid 116 is better able to fully clean and/or disinfect interior surfaces of a suction conduit, compared to a cleaning charge composed of large size water drops, or a bolus of water. The mist 116 is better able to coat and cover all interior surfaces of the conduit being cleaned, and further provides a more thorough mixture of concentrated fluid 108 and water 105.

A concentrated cleaning solution 108 may be stored at a convenient and out-of-the-way location in a storage container 109. One workable cleaning fluid 108 is an enzymatic solution, typically containing a protease enzyme, best suited for cleaning contaminants such as blood from the interior of conduits. Another operable cleaning solution is an antibacterial or surfactant material. Surfactant fluids typically are used in dental operatories performing primarily tooth cleaning and other operations producing minimal blood product. Other workable cleaning fluids 108 suitable for use in other applications include certain solvents (such as alcohol, methylene chloride, carbon tetrachloride, or others), detergents, and/or cleansers.

Container 109 generally is attached to the venturi 107 by a length of siphon 111 connected to suction opening 110. Container 109 desirably holds a quantity of concentrated cleaning fluid 108 to permit entrance of the fluid 108 into a first end 123 of siphon 111. A check valve (not illustrated) may be incorporated in a fluid flow path through siphon 111 to resist dilution of the fluid 108. The container 109 can be placed on the floor near the housing. If desired, container 109 may be part of, or contained within, housing 101. In an alternative configuration, container 109 may be held by housing 101—e.g. on a hook or shelf (not illustrated).

As illustrated in FIG. 2, discharge atomizing ports 119 and 120 are typically arranged for plug-fit reception inside conduits 125 and 127, respectively, having cooperating internal structure. Alternatively, conduits 125 and 127 may be received in a plug fit inside of atomizing ports 119 or 120. Tubes 125 and 127 generally connect on their opposite ends to high volume evacuation valves 129 and 130. With reference to FIG. 3, connector 121 receives a male end portion of tube 132, with an opposite end of tube 132 typically attached to saliva ejector valve 133.

As illustrated in FIG. 2, discharge ports 119 and 120 each typically include fluted structure 135 carried on an exterior surface 136 and operable to permit an air bypass to augment the volumetric flow through bore 137 and suctioned into an installed suction conduit, such as one or more of conduits 125 and 127. Such bypass air is entrained into the fluid 116, additionally mixes the fluid 116, and forms an effective cleaning fluid mist. Discharge ports having such air admitting structure may be regarded as atomizing discharge ports. Similarly, FIG. 3 illustrates fluted structure 139 carried on interior surface 140 of through-bore 141. Flutes 139 permit bypass air to augment the volume of cleaning fluid 116 drawn through bore 141.

It is within contemplation for valve 104 to be controlled to open either automatically or manually. As illustrated in FIG. 1, valve 104 may be actuated by a rotatable handle 144. Any sort of operable on/off valve 104 may be employed, including gate, ball, or plunger-type valves, and may also be push-button, solenoid, or toggle actuated. In one automatic, or partially automatic embodiment, the valve 104 may be activated in response to the presence of a suctioning conduit placed into a ready position coupled with a discharge port.

It is within contemplation to provide one or more occluding devices to occlude discharge ports that are not being discharged into suction conduits. Such an occluding device can be embodied as a discharge control valve (not illustrated). Such a discharge control valve may resist undesired discharge of mist 116 through certain open and unused discharge ports and into the room. Discharge control valves within contemplation can be manual, or partially or fully automated. It is within contemplation for a suctioning conduit to actuate or open such a discharge control valve upon being placed into mating reception with a discharge port, such as a discharge port 119–121. A discharge control valve may also be embodied as a cap, cork, or stopper that is configured to occlude a discharge port. An alternative discharge control valve may include an end of a suction conduit that lacks an applied internal suctioning force. Such a nonsuctioning conduit effectively operates as a stopper or cap. Unused discharge ports can effectively be used as receptacles to hold spare, extra, or unused, suction conduits and suction devices.

The device 100 may be used for cleaning the HVE system as-desired. Cleaning may be performed on an automated schedule, performed manually on-demand, or as the need arises. In one method for on-demand cleaning of a conduit system, a metering apparatus 100 is provided at a cleaning location. One convenient cleaning location for apparatus 100 is affixed to a wall. Then, a suction conduit is placed into mating reception with a discharge port of device 100. Suction is applied to the suction conduit to be cleaned, and valve 104 is opened for a time interval sufficient to clean that suction conduit. In an automated cleaning method, one or more conduits, such as a conduit 125, 127, or 132, may be placed in a stored position in engagement with a corresponding discharge port. Any, or all of valve 104 and one or more suction control valve(s) disposed to provide suction through a conduit may then be actuated according to a desired cleaning schedule. Actuation of the valves may be programmed automatically to occur as desired. Programming may be effected by mechanisms ranging from a simple timer, to a software program stored in a computer memory.

While the invention has been described in particular with reference to a certain illustrated embodiment, such is not intended to limit the scope of the invention. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus to deliver cleaning solution to a suctioning conduit, comprising:
   a first valve configured for attachment to a pressurized fluid supply and adapted to permit or resist a flow of a first fluid from said fluid supply;
   a venturi valve;
   a siphon tube:
   a container adapted to hold concentrated cleaning fluid for entrance of said concentrated cleaning fluid into a first end of said siphon tube, a second end of said siphon tube being connectable in fluid communication with a suction orifice of said venturi valve;
   a manifold defining a first volume in which to receive diluted cleaning fluid comprising a discharged mix of said first fluid and said concentrated cleaning fluid from said venturi valve; and
   a first atomizing discharge port in fluid communication with said volume in said manifold, said first atomizing discharge port comprising fluted structure carried on an exterior surface effective to admit bypass air to augment a volumetric flow suctioned into an installed first suctioning conduit and being configured and arranged to receive said first suctioning conduit for purpose of supplying said diluted cleaning fluid in misted form into said first suctioning conduit.

2. The apparatus of claim 1, further comprising:
   a second atomizing discharge port in fluid communication with said volume in said manifold, said second atomizing discharge port comprising fluted structure carried on an interior surface effective to admit bypass air to augment a volumetric flow suctioned into an installed second suctioning conduit and being configured and arranged to receive said second suctioning conduit for purpose of supplying said diluted cleaning fluid in misted form into said second suctioning conduit.

3. The apparatus of claim 1, said first valve being a manual on/off valve.

4. The apparatus of claim 1, said first valve being an automatically activated valve.

5. The apparatus of claim 4, said first valve being activated by placement of a suctioning conduit into a receiving position with respect to said discharge port.

6. The apparatus of claim 1, further comprising a housing adapted to hold said first valve, said venturi valve, and said manifold in a fixed arrangement, said housing being configured and arranged for mounting onto a suspension structure.

7. The apparatus of claim 6, wherein said suspension structure comprises a wall of a building.

8. The apparatus of claim 1, further comprising a plurality of atomizing discharge ports, each such atomizing discharge port being in fluid communication with said volume in said manifold.

9. The apparatus of claim 8, further comprising a shut-off valve disposed to occlude an atomizing discharge port.

10. The apparatus of claim 9, wherein said shut-off valve is opened, to permit flow of misted cleaning fluid therethrough, by placement of a conduit into mating reception with said discharge port.

11. The apparatus of claim 9, wherein said shut-off valve comprises a stopper configured substantially to occlude an atomizing discharge port.

12. The apparatus of claim 9, wherein said shut-off valve comprises a cap configured substantially to occlude an atomizing discharge port.

13. A method for cleaning a suction conduit, comprising the steps of:
   providing an apparatus structured according to claim 1;
   connecting said first valve to a pressurized fluid supply;
   placing said suction conduit into mating reception with said discharge port; and
   opening said first valve for a time interval sufficient to clean said suction conduit.

14. The method of claim 13, further comprising the step of opening a suction valve prior to opening said first valve, said suction valve being configured and arranged to cause a flow through said suction conduit.

15. The method of claim 14, wherein opening of said suction control valve is automatically effected according to a programmed schedule.

16. The method of claim 15, wherein opening of said first valve is automatically effected according to a programmed schedule.

17. An apparatus to deliver cleaning solution to a suctioning conduit, comprising:
   a first valve configured for attachment to a pressurized fluid supply and adapted to permit or resist a flow of a first fluid from said fluid supply;
   a venturi valve;
   a siphon tube;
   a container adapted to hold concentrated cleaning fluid for entrance of said concentrated cleaning fluid into a first end of said siphon tube, a second end of said siphon tube being connectable in fluid communication with a suction orifice of said venturi valve;
   a manifold defining a first volume in which to receive diluted cleaning fluid comprising a discharged mix of said first fluid and said concentrated cleaning fluid from said venturi valve; and
   a first atomizing discharge port in fluid communication with said volume in said manifold, said first atomizing discharge port comprising fluted structure carried on an interior surface effective to admit bypass air to augment a volumetric flow suctioned into an installed first suctioning conduit and being configured and arranged to receive said first suctioning conduit for purpose of supplying said diluted cleaning fluid in misted form into said first suctioning conduit.

18. A method for cleaning a suction conduit, comprising the steps of:
   providing an apparatus structured according to claim 17;
   connecting said first valve to a pressurized fluid supply;
   placing said suction conduit into mating reception with said discharge port; and
   opening said first valve for a time interval sufficient to clean said suction conduit.

* * * * *